United States Patent [19]

Taheri

[11] Patent Number: 4,576,180
[45] Date of Patent: Mar. 18, 1986

[54] METHOD AND APPARATUS FOR MONITORING LEG BLOOD PRESSURE OF AN AMBULATORY PATIENT

[76] Inventor: Syde A. Taheri, 268 Dan Troy, Williamsville, N.Y. 14221

[21] Appl. No.: 521,148

[22] Filed: Aug. 8, 1983

[51] Int. Cl.[4] .................................................. A61B 5/02
[52] U.S. Cl. ..................................... 128/673; 128/670
[58] Field of Search ............................ 128/672–675, 128/670, 782, 905, 900

[56] References Cited

U.S. PATENT DOCUMENTS

| | | | |
|---|---|---|---|
| 3,557,779 | 1/1971 | Weinstein | 128/677 |
| 3,581,733 | 6/1971 | Grandjean | 128/673 |
| 3,590,818 | 7/1971 | Lemole | 128/674 |
| 3,874,369 | 4/1975 | Pannier, Jr. et al. | 128/673 |
| 3,955,562 | 5/1976 | Farrar, Jr. | 128/782 |
| 3,996,926 | 12/1976 | Birnbaum | 128/673 |
| 3,996,927 | 12/1976 | Frank | 128/673 |
| 4,003,370 | 1/1977 | Emil et al. | 128/673 |
| 4,160,448 | 7/1979 | Jackson | 128/673 |
| 4,216,779 | 8/1980 | Squires et al. | 128/682 |
| 4,245,648 | 1/1981 | Trimmer et al. | 128/680 |
| 4,252,127 | 2/1981 | Gemelke | 128/680 |
| 4,314,480 | 2/1982 | Becker | 73/706 |
| 4,325,382 | 4/1982 | Miodownik | 128/673 |
| 4,347,851 | 9/1982 | Jundanian | 128/668 |
| 4,354,505 | 10/1982 | Shiga | 128/905 X |

FOREIGN PATENT DOCUMENTS

| | | | |
|---|---|---|---|
| 2315747 | 2/1977 | France | 128/673 |
| 0906515 | 2/1982 | U.S.S.R. | 128/672 |

OTHER PUBLICATIONS

Corbett et al., "Self-Levelling Central-Venous Sphygmomanometer"; Med. and Biol. Eng., vol. 12, No. 3, 5-1974, p. 366.

*Primary Examiner*—Lee S. Cohen
*Assistant Examiner*—Angela D. Sykes
*Attorney, Agent, or Firm*—Joseph P. Gastel

[57] ABSTRACT

A leg blood pressure monitor for an ambulatory patient during his normal daily activities including a catheter for insertion into a blood vessel, a pressure transducer for converting blood pressure to an electrical signal which is representative of the blood pressure, a voltage controlled oscillator for providing a frequency output which is proportional to the electrical signal, and a tape recorder for recording the frequency output and the attitude of the ambulatory patient along a time base. The tape recorder may include a microphone into which the patient dictates the attitude of various relevant parts of his body during pain episodes, or position transducers may be attached to the calf, thigh and side of the patient to produce outputs which show the attitudes of these parts of the body and which are recorded on the tape recorder with reference to the blood pressure readings. In addition, the tape recorder may include referencing mechanism to indicate on the tape the occurrences of pain episodes. A method of monitoring the blood pressure of an ambulatory patient during his normal daily activities by invasively measuring venous leg pressure in relation to the attitude of various parts of the patient's body and in relation to the occurrence of pain and discomfort.

22 Claims, 11 Drawing Figures

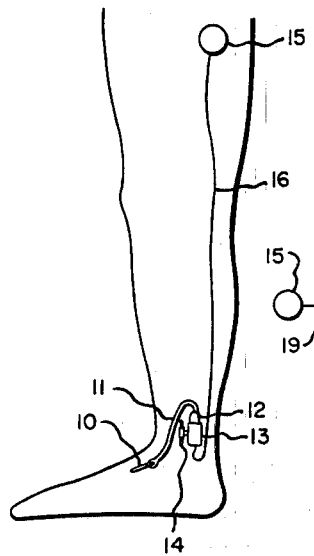
Fig. 1.
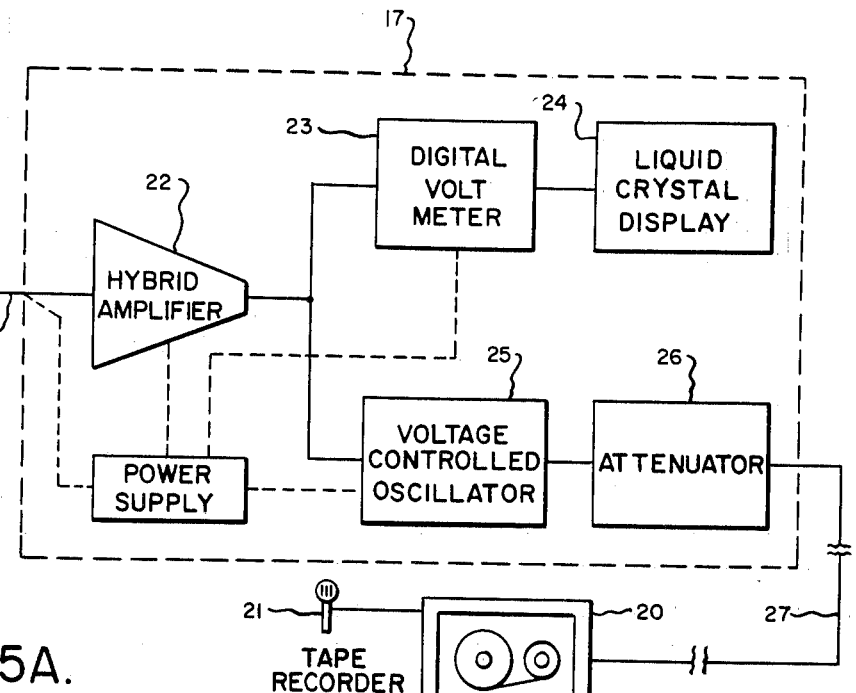
Fig. 2.
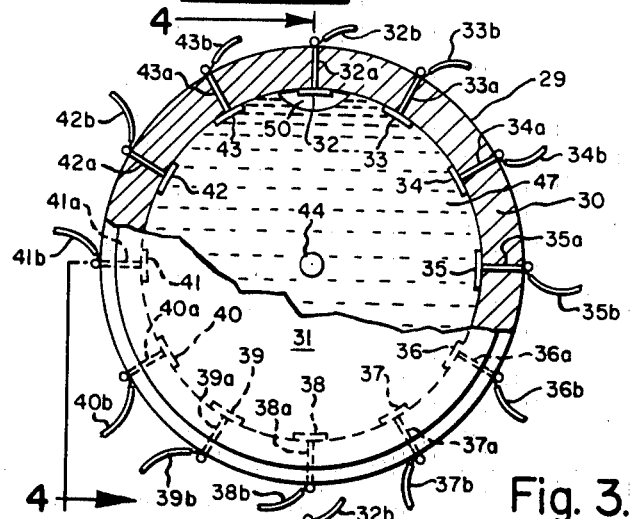
Fig. 3.
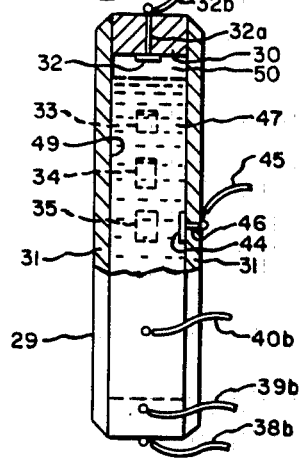
Fig. 4.
Fig. 5A.
STANDING
SIDE  - 32 AT 12 O'CLOCK
THIGH - 32 AT 12 O'CLOCK
CALF  - 32 AT 12 O'CLOCK
Fig. 5B.
SITTING
SIDE  - 32 AT 12 O'CLOCK
THIGH - 41 AT 12 O'CLOCK
CALF  - 32 AT 12 O'CLOCK
Fig. 5C.
SQUATTING
SIDE  - 32 AT 12 O'CLOCK
THIGH - 42 AT 12 O'CLOCK
CALF  - 34 AT 12 O'CLOCK
Fig. 5D.
WALKING-RUNNING
SIDE  - 32 AT 12 O'CLOCK
THIGH - 32,33,34 AT 12 O'CLOCK
CALF  - 42,43,32,33,34 AT 12 O'CLOCK
Fig. 5E.
LYING
SIDE  - 41 AT 12 O'CLOCK
THIGH - 40 AT 12 O'CLOCK
CALF  - 41 AT 12 O'CLOCK

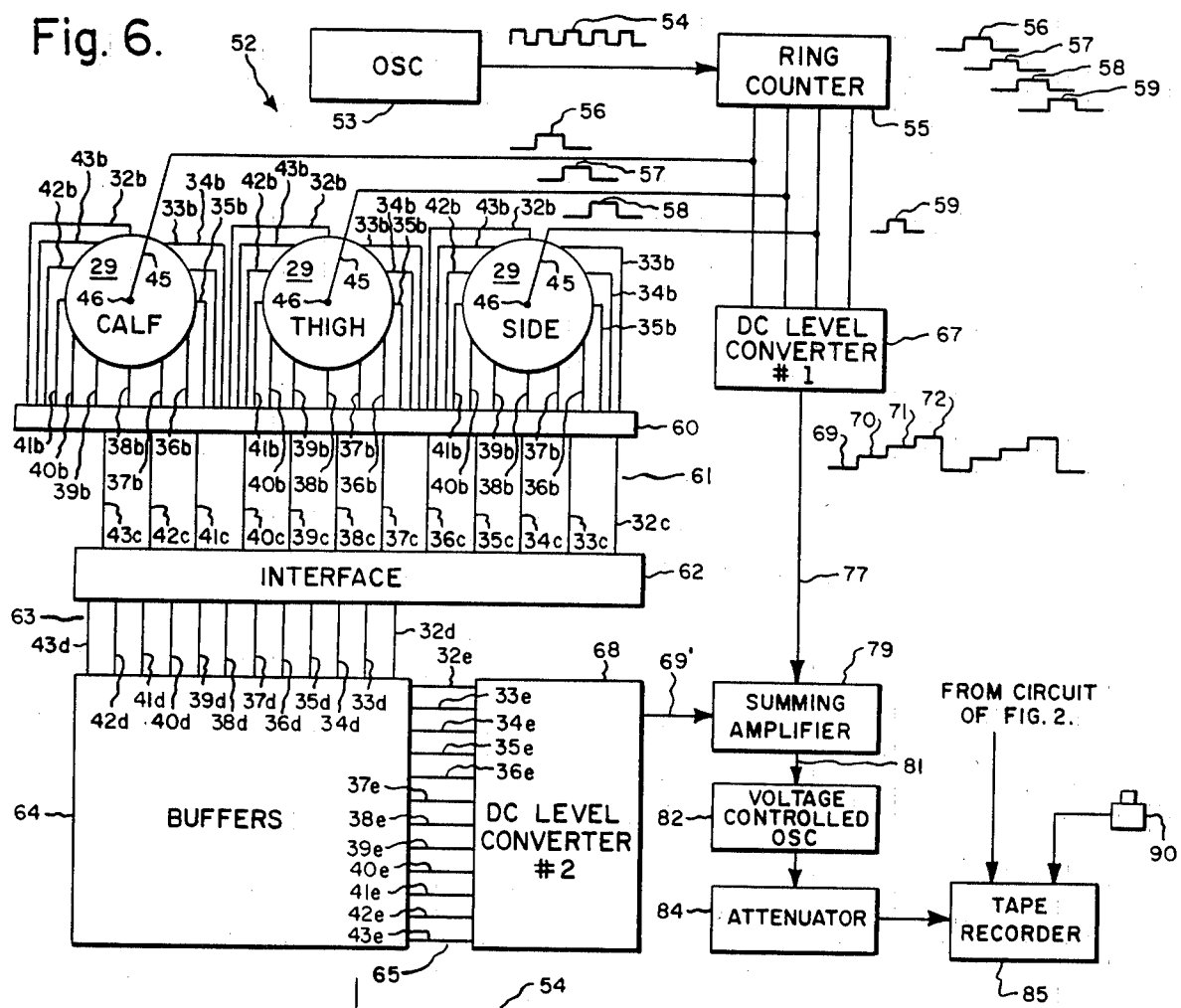
Fig. 6.
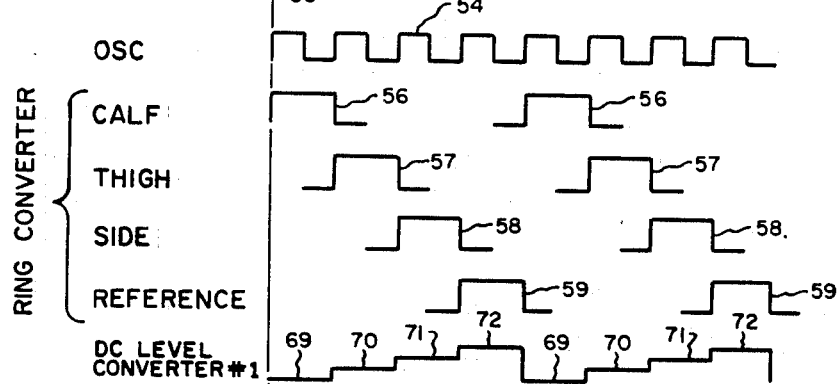
Fig. 7.
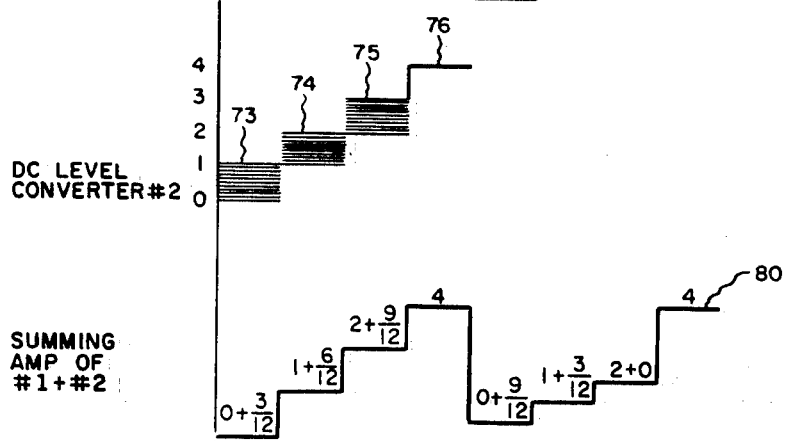

METHOD AND APPARATUS FOR MONITORING LEG BLOOD PRESSURE OF AN AMBULATORY PATIENT

BACKGROUND OF THE INVENTION

The present invention relates to a method and apparatus for invasively monitoring venous blood pressure of an ambulatory patient in relation to the attitudes of different relevant parts of the body, to thereby aid in the diagnosis of vascular disease.

By way of background, there are problems in diagnosing vascular diseases of the legs because the episodic pain and discomfort usually does not occur when the patient is being examined by the physician. For proper diagnosis, the pain and discomfort must be correlated to the attitudes of the various parts of the patient's body which might affect the venous blood pressure.

SUMMARY OF THE INVENTION

It is accordingly one important object of the present invention to provide a blood pressure monitor for an ambulatory patient which will record the blood pressure in the leg veins of a patient with reference to the activity which the patient is performing, and at the time the patient is experiencing pain or discomfort, to thereby aid in diagnosing the patient's condition.

It is another object of the present invention to provide a blood pressure monitor for an ambulatory patient which will automatically record the blood pressure in the patient's legs, and the attitude of the relevant parts of the patient's body at the time pain or discomfort is experienced.

A further object of the present invention is to provide an improved method of monitoring venous leg pressure of an ambulatory patient by correlating venous leg pressure to the attitudes of various parts of the patient's body over a period of time which includes the normal daily activities of the patient. Other objects and attendant advantages of the present invention will readily be perceived hereafter.

The present invention relates to a blood pressure monitor for monitoring the blood pressure of an ambulatory patient for a period of time which includes the normal daily activities of said patient comprising a catheter for insertion into a blood vessel, means coupled to said catheter for measuring blood pressure in said vessel, first means for recording said blood pressure, and second means for recording the attitude of at least one part of the patient's body with respect to said blood pressure in said vessel.

The present invention also relates to a method of monitoring venous leg pressure of an ambulatory patient over a period of time which includes the normal daily activities of the patient to aid in the diagnosis of vascular disease comprising the steps of inserting a catheter into a vein, measuring the venous pressure in said vein, monitoring the attitude of at least one part of the patient's body, and recording said attitude with respect to the venous pressure.

The various aspects of the present invention will be more fully understood when the following portions of the specification are read in conjunction with the accompanying drawings wherein:

BRIEF DESCRIPTION OF THE DRAWINGS

FIG. 1 is a fragmentary side elevational view of a pressure transducer mounted on the leg of a patient;

FIG. 2 is a schematic block diagram of an electronic circuit which converts the electrical signal from the pressure transducer to a frequency which is recorded on a magnetic tape of a tape recorder;

FIG. 3 is a side elevational view, partially in cross section and broken away, of a position indicator which may be attached to the calf, thigh and side of a patient for the purpose of recording the attitudes of these parts of the body;

FIG. 4 is a fragmentary cross sectional view taken substantially along line 4—4 of FIG. 3;

FIGS. 5A, 5B, 5C, 5D and 5E are charts showing the position of the bubble in the device of FIGS. 3 and 4 when the patient's calf, thigh and side are in various positions;

FIG. 6 is a schematic block diagram of an electrical circuit used in conjunction with the attitude indicators of FIGS. 3 and 4 for recording the attitude of the patient's calf, thigh and side along a time base; and FIG. 7 is a schematic diagram showing the waveforms produced by the circuit of FIG. 6.

DESCRIPTION OF THE PREFERRED EMBODIMENTS

In accordance with the present invention, the patient's saphenous vein is catheterized by a standard accepted technique. The catheter 10 which is inserted into the vein is connected to extension tubing 11 which in turn is connected to disposable dome 12 of pressure transducer 13. The dome, tubing and catheter are filled with a sterile solution, such as sterile saline solution, thus providing a liquid column between transducer 13 and catheter 10. A stop cock 14 is attached to the dome in order to provide a means of flushing the liquid column and administering an anticoagulant. The foregoing structure is conventional. Transducer 13 converts the pressure in the saphenous vein into a low level electrical signal which is conducted to connector 15 attached to the patient's thigh by electrical lead 16.

An electrical circuit 17 has a lead 19 which is selectively connected to plug 15. The circuit 17 converts signals obtained from transducer 13 into frequencies which are recorded on one track of a two-track tape of tape recorder 20. The tape recorder also includes a microphone 21, which may be of the built-in type, into which the patient dictates the attitude of his calf, thigh and side whenever he experiences pain so that this information will appear on the second track of the tape alongside the pressure indications on the first track. The tape is thereafter analyzed to correlate the vein pressure with the attitude of various parts of the patient's body when he is experiencing pain.

The circuit 17 includes a hybrid instrumentation amplifier 22 which receives the electrical signal produced by transducer 13. The signal, from hybrid amplifier 22 is converted into a digital format by digital volt meter 23 and displayed as numerical pressure information on the liquid crystal display 24. The foregoing displays are solely for use by the physician when observing the patient. However, for the purpose of recording the vein pressure, the signal from hybrid amplifier 22 is used to modulate the voltage controlled oscillator 25, thereby creating a frequency modulated signal which is attenuated by attentuator 26 and routed to one channel of tape recorder 20 through lead 27. Both the electrical circuit 17 and the tape recorder 20 are carried in a shoulder strap bag. The transducer 13 is taped to the patient's ankle.

The frequency modulated signal which has been recorded on the one channel of the tape is interpreted by converting the frequency to a pressure reading and, when this pressure reading is compared to the positions of the various relevant parts of the patient's body, the physician can use this information in diagnosing vascular problems.

In FIGS. 3-7 an automatic patient-position indicator and recording circuit are shown. This will obviate the necessity for the patient to use microphone 21 to record relevant data including his position and the experiencing of pain. The position transducer 29 of the circuit comprises a disc-like member having an annular wall 30 which is positioned in sealed relationship to side walls 31. The position transducer 29 includes twelve metal contacts 32 through 43, inclusive, which are equally spaced at 30° from each other with contact 32 being located at a 12 o'clock position. Each of the contacts 32 through 43 is connected to leads 32b through 43b, respectively, by metal pins 32a through 43a, inclusive, respectively. An additional contact 44 is positioned at the center of one of the sides 31 and is connected to lead 45 by pin 46. The position transducer 29 is filled with a conductive liquid or electrolyte 47 which fills the chamber 49 completely except for air bubble 50. The volume of air bubble 50 is such that it can completely surround any one of the metal contacts 32-43, inclusive, at any given time but it cannot surround two of these contacts at any one time.

Preferably, three transducers are used. One position transducer 29 is attached to the side of the patient's calf by tape; another transducer 29 is attached to the side of the patient's thigh with tape; and a third transducer 29 is secured to the patient's side above the hip with tape. The three transducers will be positioned so that contact 32 is at the 12 o'clock position when the patient is standing, as shown in FIG. 5A so that the air bubble 50 will surround contact 32 in each transducer 29. When the patient is sitting, as shown in FIG. 5B, contact 32 of the side transducer 29 will remain in the 12 o'clock position and thus will be surrounded by air bubble 50. However, at this time the thigh transducer 29 will be located with contact 41 at the 12 o'clock position and thus contact 41 will be surrounded by bubble 50, and the calf transducer 29 will be positioned with contact 32 in the 12 o'clock position. When the patient is squatting, as shown in FIG. 5C, the side transducer 29 will be positioned with contact 32 at the 12 o'clock position, the thigh transducer will be positioned with contact 42 at the 12 o'clock position, and the calf transducer will be positioned with contact 34 at the 12 o'clock position. When the patient is walking or running, as shown in FIG. 5D, contact 32 of the side transducer will be at the 12 o'clock position, the thigh transducer will fluctuate so that contacts 32, 33 and 34 will sequentially occupy the 12 o'clock position, and the calf transducer will fluctuate so that contacts 42, 43, 32, 33 and 34 will periodically occupy the 12 o'clock position. From FIG. 5E it can be seen that when the patient is lying in the position depicted therein, the side transducer 29 will be oriented with contact 41 at the 12 o'clock position, the thigh transducer will be oriented with contact 40 at the 12 o'clock position and the calf transducer will be oriented with contact 41 at the 12 o'clock position. In all of the foregoing orientations, the contact which is located in the 12 o'clock position will be surrounded by the air bubble and thus there cannot be a flow of electrical current from that contact and central contact 44 through the conductive liquid 47. However, it will be appreciated that less than three transducers can be used. For example, under certain conditions it might be desirable to measure only the attitude of the calf and thigh, or possibly the thigh and side, or possibly only the thigh or calf.

An electronic circuit 52 of FIG. 6 is associated with transducers 29 to record the positions of the transducers on a time base. This can be done because the impedance between the contact surrounded by the air bubble and central contact 44 is much greater than the impedance between the remainder of the contacts and the central contact 44. The electrical circuit includes an oscillator 53 which generates a square wave 54 (FIGS. 6 and 7). The output of oscillator 53 is conducted to ring counter 55 which will generate a square wave every time the pulse from oscillator 53 goes positive. Thus, four square waves 56, 57, 58 and 59 will be generated in sequence and then the cycle will be repeated. Square waves 56, 57 and 58 are conducted to the central contacts 44 of the calf, thigh and side position transducers 29, respectively. Square wave 59 is conducted directly to DC level converter 1 to serve as a time reference.

As can be seen from FIG. 6, the leads 32b-43b of each position transducer 29 are conducted to a bus bar 60 so that leads with corresponding numerals will be attached to the same conductor. Thus, the thirty-six leads entering bus bar 60 will be connected to twelve terminals, with each terminal attached to three leads designated by the same numeral. Twelve leads 32c to 43c, inclusive, will leave bus bar 60 at 61, with each of the leads 32c-43c, inclusive, essentially being connected to each of the three corresponding leads having the same numeral with the suffix b entering bus bar 60. For example, lead 32c at 61 will be connected to the three leads 33b entering bus bar 60, another lead 33b at 61 will be connected to three leads 43b entering bus bar 60, etc. The leads 32c-43c, inclusive, at 61 will be coupled to interface 62 which compensates for temperature variations, electrolyte differences, and other factors to provide a clean signal in each of the twelve leads at 63 leaving interface 62. The twelve leads 32d-43d, inclusive, at 63 will couple the output of interface 62 to buffers 64 which will provide voltages at output leads 33e-43e, inclusive, at 65 which are inverse to the input voltages from the twelve leads at 63, leads 32e-43e, inclusive, being coupled to leads 32d-43d, inclusive, respectively, entering the buffer. More specifically, for all of the contacts 32-43, inclusive, of each position transducer 29 which are coupled to central contact 44 through electrolyte 47, there will be a high signal input to buffers 64 and consequently there will be a low voltage output at leads 65. Conversely, for the particular contact 32-43 which is being surrounded by air bubble 50, there will be a low input to buffers 64 through the leads at 63 and consequently there will be a high voltage output at the appropriate leads at 65. Thus, at the leads at 65 there will only be one high voltage output from each position transducer 29 at any given time. Furthermore, as noted previously, each of the twelve leads 32e-43e, inclusive, at 65 will be coupled to the contact of each of the position transducers 29 having the same common digits. For example, lead 32e of the leads at 65 will effectively be coupled to all contacts 32 of each position transducer 29 through leads 32d, 32c and 32b. Another of the leads 43e at 65 will be coupled to all contacts 43 of all of the three transducers 29 through leads 43d, 43c and 43b, etc.

The DC level converter No. 1 at 67 produces a stepped output wherein voltage level 69 is representative of calf transducer 29, voltage level 70 is representative of thigh transducer 29, voltage level 71 is representative of side transducer 29, and voltage level 72 represents a time signal. DC level converter No. 2 can produce a range of voltage outputs 73, 74, 75 and 76 (FIG. 7). For example, voltage level 73 may range from 0 to 1 volt in twelve equal increments of 1/12th volt. Voltage level 74 may range between 1 and 2 volts in equal increments of 1/12th volt. Voltage level 75 may range between 2 and 3 volts in equal increments of 1/12th volt, and voltage level 76 ranges will always be 4 volts. Each of the like-numbered leads 32b–43b, inclusive, of each of the position transducers 29 is essentially coupled to a respective one of the twelve leads at 65 leaving buffers 64. The DC level converter No. 2 at 68 is essentially a solid state voltage divider which will output voltages in 1/12th of 1 volt increments. Therefore, for example, if the contact 32 at one of the position transducers 29 is located at the bubble 50, one of the leads at 65 which will correspond to the contact 32 will conduct and there will be a corresponding output at 69′ from the DC level converter 68. In short, DC level converter 68 will provide an output at a voltage level which corresponds to each of the twelve contacts 32-43 of each of the position transducers 29. The output of DC level converter 69 and the output from DC level converter No. 1 at 77 are fed to summing amplifier 79 which adds the voltages to provide a curve 80. Thus, for example, the voltage reading corresponding to the position of the calf might be 0 plus 3/12ths. The voltage level for corresponding to the position of the thigh might be 1 plus 6/12th. The voltage level for the position corresponding to the side might be 2 plus 9/12ths. The voltage for the time reference will always be 4. During the next cycle, as depicted on curve 80, the voltage level for the calf might be 0 plus 9/12ths; the voltage corresponding to the position of the thigh might be 1 plus 3/12ths, and the voltage corresponding to the position of the side might be 2 plus 0/12ths, and the reference voltage will be 4. The output 81 is coupled to voltage controlled oscillator 82 which produces a frequency modulated voltage which is proportional to the voltages produced by the summing amplifier to thereby produce different tones. The output of voltage controlled oscillator 82 is conducted to attentuator 84 and the output therefrom is conducted to tape recorder 85. The tones are recorded on one track. The second track receives the pressure information from a circuit 17 of FIG. 2 so that the pressure information and the patient attitude information are recorded side-by-side on two tracks.

In use, after the transducers have been positioned on the patient, the tape recorder 85 is started and the time of starting is recorded. Since pulses 59, which provide a time reference, occur at known predetermined intervals, the time which has elapsed from the time of starting the tape recorder, can be measured by counting the pulses and thus the information which is provided by the tape recorder 85 is the patient's venous pressure in reference to the attitude of the patient's calf, thigh and side at a given time. This information is especially desirable if the patient is sleeping and cannot indicate the time at which pains or discomfort occurred. Furthermore, the tape recorder has a referencing button 90 which the patient can push whenever he is experiencing discomfort or pain.

The information from the two track tape of the tape recorder is retrieved by the use of a retrieval computer, which has programmed software. The computer can search out those areas at which the referencing button was pushed or where the pressure was high, or where the patient was in certain attitudes. In addition, the computer can give a readout for a predetermined time interval before a specific event and for a given time after the specific event so that episodic pain occurrences can be correlated with vein pressure and body attitude against a time base.

While the foregoing description has referred to the position transducer being located on the patient's side, it will be appreciated that this is intended to include the positioning of this transducer on the abdomen or any other portion of the torso which will give the required intelligence.

It can thus be seen that the blood pressure monitor for an ambulatory patient as described above is manifestly capable of achieving the above enumerated objects, and while preferred embodiments of the present invention have been disclosed, it will be understood that the present invention is not limited thereto but may be otherwise embodied within the scope of the following claims.

What is claimed is:

1. A blood pressure monitor for monitoring the venous blood pressure in the leg of an ambulatory patient for a period of time which includes the normal daily activities of said patient to aid in the diagnosis of vascular disease of the leg comprising a catheter for insertion into a venous blood vessel in the leg, means coupled to said catheter for measuring blood pressure in said venous blood vessel, first means for recording said blood pressure, and second means associated with said first means for recording the attitude of at least one of the patient's leg, thigh and side with respect to said blood pressure in said venous blood vessel in the leg to thereby correlate said attitude with said blood pressure.

2. A blood pressure monitor for an ambulatory patient as set forth in claim 1 wherein said means coupled to said catheter comprises a pressure transducer means for converting said blood pressure to an electrical signal which is representative of the blood pressure, means for providing a frequency output which is proportional to said electrical signal, and wherein said first means includes means for recording said frequency output to thereby provide a record of blood pressure output.

3. A blood pressure monitor for an ambulatory patient as set forth in claim 1 wherein said second means comprises a plurality of position transducers.

4. A blood pressure monitor for an ambulatory patient as set forth in claim 1 wherein said second means comprises a position transducer means for attachment to at least one of said patient's leg, thigh or side to provide intelligence as to said attitude.

5. A blood pressure monitor for an ambulatory patient as set forth in claim 4 wherein said second means includes a position transducer means for attachment to the calf of said patient.

6. A blood pressure monitor for an ambulatory patient as set forth in claim 5 wherein said second means includes a second position transducer means for attachment to the thigh of said patient.

7. A blood pressure monitor for an ambulatory patient as set forth in claim 6 wherein said second means includes means a third position transducer means for attachment to the side of said patient.

8. A blood pressure monitor for an ambulatory patient as set forth in claim 4 wherein said second means includes a position transducer means for attachment to the thigh of said patient.

9. A blood pressure monitor for an ambulatory patient as set forth in claim 8 wherein said second means includes a second position transducer means for attachment to the side of said patient.

10. A blood pressure monitor for an ambulatory patient as set forth in claim 4 wherein said second means includes a position transducer means for attachment to the side of said patient.

11. A blood pressure monitor for an ambulatory patient as set forth in claim 1 wherein said second means include means for recording the time of occurrence of pain episodes with reference to said record of blood pressure and the attitude of said at least one of said patient's, leg, thigh and side.

12. A blood pressure monitor as set forth in claim 1 wherein said second means comprises a tape recorder means for recording said attitude by describing it by voice during the occurrence of pain episodes.

13. A blood pressure monitor as set forth in claim 1 wherein said second means comprises a tape recorder, and tape recorder referencing means for indicating the time of occurrence of pain on said tape.

14. A method of monitoring venous leg pressure of an ambulatory patient over a period of time which includes the normal daily activities of the patient to aid in the diagnosis of vascular disease of the leg comprising the steps of inserting a catheter into a vein in the patient's leg, measuring the venous pressure in said vein in said patient's leg, and monitoring the attitude of at least one of the patient's leg, thigh and side, and recording said attitude with respect to said venous pressure to thereby correlate said attitude with said venous pressure.

15. A method as set forth in claim 14 wherein said monitoring said at least one of said patient's leg, thigh and side includes the step of monitoring the attitude of said patient's thigh.

16. A method as set forth in claim 15 wherein said monitoring said at least one of said patient's leg, thigh and side includes the step of monitoring the attitude of said patient's side.

17. A method as set forth in claim 14 wherein said catheter is inserted into a vein proximate the patient's ankle.

18. A method as set forth in claim 17 wherein said monitoring said at least one of said patient's leg, thigh and side includes the step of monitoring the attitude of said patient's leg.

19. A method as set forth in claim 18 wherein said monitoring said at least one of said patient's leg, thigh and side includes the step of monitoring the attitude of said patient's thigh.

20. A method as set forth in claim 19 wherein said monitoring said at least one of said patient's leg, thigh and side includes the step of monitoring the attitude of said patient's side.

21. A method as set forth in claim 17 including the step of recording the occurrence of pain with respect to said attitude.

22. A method as set forth in claim 14 including the step of recording the occurrence of pain with respect to said attitude.

* * * * *

UNITED STATES PATENT AND TRADEMARK OFFICE
CERTIFICATE OF CORRECTION

PATENT NO. : 4,576,180
DATED : March 18, 1986
INVENTOR(S) : Syde A. Taheri

It is certified that error appears in the above—identified patent and that said Letters Patent are hereby corrected as shown below:

Column 7, line 1 (claim 7), cancel "means" (first occurrence).

Signed and Sealed this

Twenty-fourth Day of June 1986

[SEAL]

Attest:

DONALD J. QUIGG

Attesting Officer

Commissioner of Patents and Trademarks